United States Patent
Borgmeier et al.

(10) Patent No.: US 7,253,310 B2
(45) Date of Patent: Aug. 7, 2007

(54) PREPARATION OF (METH)ACRYLIC ACID

(75) Inventors: Frieder Borgmeier, Mannheim (DE);
Frank Rosowski, Mannheim (DE);
Hans-Guenther Lintz, Karlsruhe (DE);
Ina Grisstede, Karlsruhe (DE);
Elisabet Bacells Cabre, Karlsruhe (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 302 days.

(21) Appl. No.: 10/920,428

(22) Filed: Aug. 18, 2004

(65) Prior Publication Data
US 2005/0043567 A1    Feb. 24, 2005

Related U.S. Application Data

(60) Provisional application No. 60/496,015, filed on Aug. 19, 2003.

(30) Foreign Application Priority Data
Aug. 19, 2003 (DE) ............................... 103 38 529

(51) Int. Cl.
*C07C 51/16* (2006.01)
(52) U.S. Cl. ..................................... 562/542
(58) Field of Classification Search ............... 562/523, 562/542, 549
See application file for complete search history.

(56) References Cited

U.S. PATENT DOCUMENTS

| | | | |
|---|---|---|---|
| 4,297,247 A | 10/1981 | Krabetz et al. | |
| 5,677,261 A | 10/1997 | Tenten et al. | |
| 5,739,391 A | 4/1998 | Ruppel et al. | |
| 5,821,390 A | 10/1998 | Ruppel et al. | |
| 5,910,608 A | 6/1999 | Tenten et al. | |
| 6,063,728 A | 5/2000 | Hinago et al. | |
| 6,063,880 A | 5/2000 | Winter et al. | |
| 6,143,906 A | 11/2000 | Streicher et al. | |
| 6,169,214 B1 | 1/2001 | Tenten et al. | |
| 6,395,936 B1 | 5/2002 | Arnold et al. | |
| 6,403,829 B1 | 6/2002 | Unverricht et al. | |
| 6,610,629 B2 | 8/2003 | Hinago et al. | |
| 6,867,328 B2 * | 3/2005 | Borgmeier et al. | 562/598 |
| 6,998,504 B1 * | 2/2006 | Unverricht et al. | 562/545 |
| 7,012,157 B2 | 3/2006 | Borgmeier et al. | |
| 2003/0088124 A1 | 5/2003 | Dubois | |

(Continued)

FOREIGN PATENT DOCUMENTS

DE    198 35 247    2/1999

(Continued)

OTHER PUBLICATIONS

Derwent Publications, JP 2000-256257, Sep. 19, 2000.

(Continued)

*Primary Examiner*—Karl Puttlitz
(74) *Attorney, Agent, or Firm*—Oblon, Spivak, McClelland, Maier & Neustadt, P.C.

(57) ABSTRACT

A process for preparing (meth)acrylic acid by heterogeneously catalyzed gas phase partial oxidation of a saturated hydrocarbon precursor compound, in which the charging gas mixture contains from 5 to 25% by volume of steam and the molar ratio of molecular oxygen present in the charging gas mixture to saturated hydrocarbon precursor compound present in the charging gas mixture is from 1.5:1 to 2.5:1.

22 Claims, 1 Drawing Sheet

U.S. PATENT DOCUMENTS

| | | | |
|---|---|---|---|
| 2003/0187298 A1 | 10/2003 | Borgmeier et al. |
| 2004/0054222 A1 | 3/2004 | Felder et al. |
| 2004/0063988 A1 | 4/2004 | Hechler et al. |
| 2004/0082810 A1 | 4/2004 | Borgmeier et al. |
| 2004/0092768 A1 | 5/2004 | Borgmeier et al. |
| 2004/0097368 A1 | 5/2004 | Borgmeier et al. |
| 2004/0102648 A1 | 5/2004 | Borgmeier et al. |
| 2004/0138500 A1 | 7/2004 | Borgmeier |
| 2004/0199001 A1 | 10/2004 | Schindler et al. |
| 2004/0204607 A1 | 10/2004 | Machhammer et al. |

FOREIGN PATENT DOCUMENTS

| | | |
|---|---|---|
| DE | 100 29 338 | 1/2002 |
| DE | 100 46 672 | 3/2002 |
| DE | 100 51 419 | 4/2002 |
| DE | 101 22 027 | 5/2002 |
| DE | 101 45 958 | 5/2002 |
| DE | 101 18 814 | 10/2002 |
| DE | 101 19 933 | 10/2002 |
| DE | 102 54 278 | 2/2004 |
| DE | 102 46 119 | 4/2004 |
| DE | 102 54 279 | 6/2004 |
| DE | 103 16 039 | 10/2004 |
| DE | 103 16 465 | 10/2004 |
| EP | 0 529 853 | 3/1993 |
| EP | 0 603 836 | 6/1994 |
| EP | 0 608 838 | 8/1994 |
| EP | 0 895 809 | 2/1999 |
| EP | 0 962 253 | 12/1999 |
| EP | 1 080 784 | 3/2001 |
| EP | 1 090 684 | 4/2001 |
| EP | 1 123 738 | 8/2001 |
| EP | 1 180 508 | 2/2002 |
| EP | 1 192 982 | 4/2002 |
| EP | 1 192 983 | 4/2002 |
| EP | 1 192 986 | 4/2002 |
| EP | 1 192 987 | 4/2002 |
| EP | 1 192 988 | 4/2002 |
| EP | 1 193 240 | 4/2002 |
| EP | 1 238 960 | 9/2002 |
| EP | 1 254 706 | 11/2002 |
| EP | 1 254 707 | 11/2002 |
| EP | 1 254 709 | 11/2002 |
| JP | 7-232071 | 9/1995 |
| JP | 7-315842 | 12/1995 |
| WO | WO 02/06199 | 1/2002 |
| WO | WO 02/081421 | 10/2002 |

OTHER PUBLICATIONS

Derwent Publications, JP 10-036311, Feb. 10, 1998.

Derwent Publications, JP 2000-143244, May 23, 2000.

Kenji Nomiya, et al., "Anderson-Type Heteropolyanions of Molybdenum(VI) and Tungsten(VI)", Polyhedron, vol. 6, No. 2, 1987, pp. 213-218.

W. Ueda, et al., "Selective Oxidation of $C_1$-$C_3$ Alkanes over Molybdenum- and Vanadium-based Oxide Catalysts", Kinetics and Catalysis, vol. 40, No. 3, 1999, pp. 401-404.

* cited by examiner

PREPARATION OF (METH)ACRYLIC ACID

The present invention relates to a process for preparing (meth)acrylic acid by heterogeneously catalyzed gas phase partial oxidation of at least one saturated hydrocarbon precursor compound, by charging a catalyst bed which is disposed in a reactor and whose catalytically active composition is a multimetal oxide which contains the elements Mo and V, at least one of the elements Te and Sb, and at least one of the elements from the group consisting of Nb, Ta, W, Ce and Ti, and whose x-ray diffractogram has reflections h, i and k whose peak locations are at the reflection angles (2Θ) 22.2±0.5° (h), 27.3±0.5° (i) and 28.2±0.5° (k), where the reflection h is the most intense within the x-ray diffractogram and has a half-height width of at most 0.5°, the intensity $P_i$ of the reflection i and the intensity $P_k$ of the reflection k satisfy the relationship $0.55 \leq R \leq 0.85$ in which R is the intensity ratio defined by the formula $$R = P_i/(P_i + P_k)$$

and the half-height width of the reflection i and of the reflection k are each $\leq 1°$, at elevated temperature with a charging gas mixture which, in addition to the at least one saturated hydrocarbon precursor compound, molecular oxygen as an oxidant and steam as a promoter, also comprises at least one diluent gas which is substantially inert under the conditions of the heterogeneously catalyzed gas phase partial oxidation.

In this document, the notation (meth)acrylic acid is an abbreviation of methacrylic acid or acrylic acid.

(Meth)acrylic acid forms reactive monomers which are suitable, for example, for preparing polymers which may find use, inter alia, as adhesives.

On the industrial scale, (meth)acrylic acid can be prepared, inter alia, by heterogeneously catalyzed gas phase partial oxidation of propane or isobutane.

By heterogeneously catalyzed partial gas phase oxidation of a mixture of propane and isobutane, acrylic acid and methacrylic acid may be obtained in a mixture.

Propane and isobutane are therefore referred to in this document as saturated hydrocarbon precursor compounds of (meth)acrylic acid.

BACKGROUND OF THE INVENTION

Processes for preparing (meth)acrylic acid by heterogeneously catalyzed gas phase partial oxidation of at least one saturated hydrocarbon precursor compound, by charging a catalyst bed which is disposed in a reactor and whose catalytically active composition is a multimetal oxide which contains the elements Mo and V, at least one of the elements Te and Sb, and at least one of the elements from the group consisting of Nb, Ta, W and Ti, and whose x-ray diffractogram has reflections h, i and k whose peak locations are at the reflection angles (2Θ) 22.2±0.5° (h), 27.3±0.5° (i) and 28.2±0.5° (k) at elevated temperature with a charging gas mixture which, in addition to the at least one saturated hydrocarbon precursor compound, molecular oxygen as an oxidant and steam as a promoter, also comprises at least one diluent gas which is substantially inert under the conditions of the heterogeneously catalyzed gas phase partial oxidation, are known (cf., for example, EP-A 1192987, DE-A 10122027, JP-A 2000-256257, EP-A 608838, EP-A 1193240, EP-A 1238960, EP-A 962253, JP-A 10-36311 and EP-A 1254706).

According to the teaching of these prior art documents, it is particularly advantageous that steam is present in the charging gas mixture, since, inter alia, it promotes the selectivity of (meth)acrylic acid formation (cf., for example, EP-B 608838 page 4), and according to the teaching of the prior art, an increasing amount of steam in the charging gas mixture has an increasingly advantageous effect. The activity of the catalytically active multimetal oxide composition is also favorably influenced by the presence of steam.

It is also known of the catalytically active multimetal oxide compositions used that the catalyzed partial oxidation is brought about by the oxygen present in the multimetal oxide active compositions, and has to be constantly resupplied to the multimetal oxide active composition by way of a redox reaction by means of the molecular oxygen present in the charging gas mixture.

Increased molar ratios of molecular oxygen to saturated hydrocarbon precursor compound in the charging gas mixture are therefore generally regarded as advantageous.

However, a disadvantage of the aforementioned procedures which are recommended as particularly advantageous is that the (meth)acrylic acid does not occur as a pure substance in the product gas of the heterogeneously catalyzed partial gas phase oxidation but rather as a constituent of a mixture from which the (meth)acrylic acid has to be removed (cf., for example, DE-A 10316465). However, as a consequence of the high affinity of (meth)acrylic acid to water, a separation of (meth)acrylic acid from steam present in the product gas mixture is particularly energy-intensive. It would therefore be advantageous from this aspect for the steam fraction in the charging gas mixture to be very low.

A further point is that the reaction gas mixture, as it passes through the catalyst bed, has to overcome its resistance. The energy required for this purpose has to be supplied to the charging gas mixture beforehand (for example in the form of compressive work; however, the reaction gas mixture may in principle also be sucked through the catalyst bed).

It will be appreciated that the greater the amount of the charging gas mixture, the greater the total amount of work to be performed (especially when conducting cycle gas). From this aspect, not only would a small steam content be advantageous, but also a very low ratio of molecular oxygen present in the charging gas mixture to the saturated hydrocarbon precursor compound present in the charging gas mixture. This is all the more true when the oxygen source used is not pure oxygen or nitrogen-depleted air, but rather air itself, since each oxygen molecule in this case is additionally accompanied by four nitrogen molecules.

It would therefore be advantageous for a process for heterogeneously catalyzed gas phase partial oxidation of at least one saturated hydrocarbon precursor compound to (meth)acrylic acid to display its full performance even at comparatively low steam contents of the charging gas mixture and comparatively small molar ratios of molecular oxygen present in the charging gas mixture to the at least one saturated hydrocarbon precursor compound in the charging gas mixture.

It is now generally known that catalytically active multimetal oxides which contain the elements Mo and V, at least one of the elements Te and Sb, and at least one of the elements from the group consisting of Nb, Ta, W, Ce and Ti may occur in various crystalline phases (cf., for example, DE-A 10246119 and DE-A 10254279).

One of the possible crystalline phases, known as the k phase (with hexagonal structure) features an x-ray diffractogram which has high-intensity reflections at the 2Θ peak locations 22.1±0.5°, 28.2±0.5°, 36.2±0.5°, 45.2±0.5° and 50.0±0.3°.

A second specific crystal structure (orthorhombic structure) in which the relevant multimetal oxide active compositions may occur is generally referred to as the i phase. Its x-ray diffractogram features, inter alia, high-intensity reflections at the 2Θ peak locations 22.2±0.5°, 27.3±0.5° and 28.2±0.5°, but, in contrast to the k phase, does not exhibit a high-intensity reflection at the 2Θ peak location 50.0±0.3° (cf. DE-A10119933 and DE-A 10118814).

The customary preparative processes of the relevant multimetal oxide compositions (for example the preparative processes of EP-A 1192987, EP-A 529853 and EP-A 603836) normally provide neither pure k phase nor pure i phase, but rather mixed crystal structures which are an intertwined mixture of k and i phase in which the k phase fraction normally dominates.

A measure of the i phase fraction in these mixed crystal structures is the intensity ratio $$R=P_i/(P_i+P_k)$$

where $P_i$ is the intensity of the reflection i at 2Θ=27.3±0.5° and $P_k$ is the intensity of the reflection k at 2Θ=28.2±0.5° in the corresponding x-ray diffractogram.

Particularly high i phase fractions are present when 0.55 or 0.65≦R≦0.85. Pure i phase is present when the 2Θ peak location, 50.0±0.3°, additionally exhibits no reflection (cf., for example, DE-A 10246119).

Increased i phase fractions can be generated, inter alia, by washing the mixed crystal structures containing k and i phase with suitable liquids, for example aqueous nitric acid.

DETAILED DISCUSSION OF THE INVENTION

Figure 1:
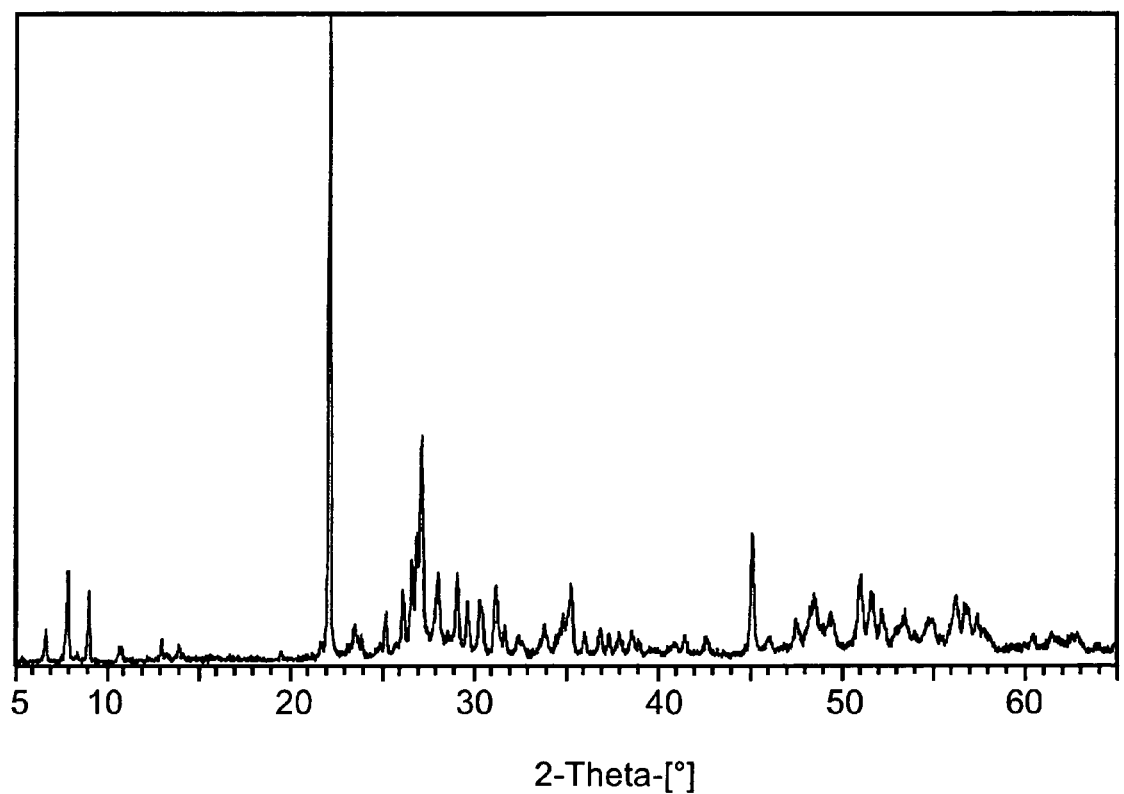
FIG. 1 shows the x-ray diffractogram of the active composition in the tables prepared in Example (A).

It has been found in accordance with the invention that, surprisingly, the performance (activity and selectivity with respect to the target compound) of multimetal oxide active compositions containing the elements Mo and V, at least one of the elements Te and Sb, and at least one of the elements from the group consisting of Nb, Ta, W and Ti, and having an increased i phase fraction, with respect to the heterogeneously catalyzed gas phase partial oxidation of at least one saturated hydrocarbon precursor compound to (meth)acrylic acid, within wide ranges, is substantially independent of the steam fraction present in the charging gas mixture and molar ratio of molecular oxygen to saturated hydrocarbon precursor compound.

As a solution to the problems of the prior art processes, a process has been found for preparing (meth)acrylic acid by heterogeneously catalyzed gas phase partial oxidation of at least one saturated hydrocarbon precursor compound, by charging a catalyst bed which is disposed in a reactor and whose catalytically active composition is a multimetal oxide which contains the elements Mo and V, at least one of the elements Te and Sb, and at least one of the elements from the group consisting of Nb, Ta, W, Ce and Ti, and whose x-ray diffractogram has reflections h, i and k whose peak locations are at the reflection angles (2Θ) 22.2±0.5° (h), 27.3±0.5° (i) and 28.2±0.5° (k), where the reflection h is the most intense within the x-ray diffractogram and has a half-height width of at most 0.5°, the intensity $P_i$ of the reflection i and the intensity $P_k$ of the reflection k satisfy the relationship 0.55≦R≦0.85 in which R is the intensity ratio defined by the formula $$R=P_i/(P_i+P_k)$$

and the half-height width of the reflection i and of the reflection k are each ≦1°, at elevated temperature with a charging gas mixture which, in addition to the at least one saturated hydrocarbon precursor compound, molecular oxygen as an oxidant and steam as a promoter, also comprises at least one diluent gas which is substantially inert under the conditions of the heterogeneously catalyzed gas phase partial oxidation, wherein the steam content of the charging gas mixture is from 5 to 25% by volume and the molar ratio V of molecular oxygen present in the charging gas mixture to the at least one saturated hydrocarbon precursor compound present in the charging gas mixture is from 1.5:1 to 2.5:1.

In the process according to the invention, inert diluent gases refer to gases which differ from molecular oxygen, steam and the at least one saturated hydrocarbon precursor compound, and of which at least 95 mol % and most preferably 100 mol % remain chemically unchanged on single pass of the charging gas mixture through the catalyst bed.

Together with the steam, the inert diluent gases are capable of absorbing heat of reaction released with their heat capacity and at the same time favorably influencing the explosion behavior of the charging gas mixture (starting reaction gas mixture). They also typically exert an advantageous influence on the reaction rate. Typically, the inert diluent gases used are noncombustible gases.

One of the most frequently used inert diluent gases is molecular nitrogen which is automatically used when the oxygen source used for the heterogeneously catalyzed gas phase partial oxidation according to the invention is air.

In many cases, a cycle gas is also used as an inert diluent gas (cf., for example, DE-A 10316039 or EP-A 1180508). Cycle gas refers to the residual gas which remains in the heterogeneously catalyzed gas phase partial oxidation of at least one organic precursor compound when the target product, (meth)acrylic acid, has been separated more or less selectively (for example by absorption into a suitable solvent) from the product gas mixture. In general, it consists predominantly of the inert diluent gases used for the heterogeneously catalyzed gas phase partial oxidation, steam and carbon oxides formed by undesired complete secondary oxidation. In general, it also contains unconverted reactants, i.e. propane and molecular oxygen, and also in some cases intermediates such as propene and/or acrolein.

Preference is given in accordance with the invention to using exclusively air as the oxygen source (disregarding molecular oxygen present in the cycle gas).

Moreover, the steam fraction in the charging gas mixture, in accordance with the invention, is preferably from 10 to 20% by volume. It may also be from 6 to 20% by volume or from 7 to 15% by volume. Also, the molar ratio V of molecular oxygen present in the charging gas mixture to the at least one saturated hydrocarbon compound present in the charging gas mixture, in accordance with the invention, is preferably from 1.75:1 to 2.25:1. However, it may also be from 1.8 to 2.3.

It is particularly advantageous in accordance with the invention for the aforementioned preferred configuration variants of the charging gas mixture in the process according to the invention to be satisfied simultaneously.

Preference is also given in accordance with the invention to $0.65 \leq R \leq 0.85$ or $0.67 \leq R \leq 0.75$ and very particular preference to R=from 0.69 to 0.75 or R=from 0.71 to 0.74 or 0.73, or R=0.72. This is also particularly advantageously true in the particularly advantageous configurations of the charging gas mixture.

In addition to the reflections h, i and k, the x-ray diffractogram of the catalytically active multimetal oxide compositions to be used in accordance with the invention generally also contains further reflections whose peak locations are at the following reflection angles (2Θ):

9.0±0.4° (l),
6.7±0.4° (o) and
7.9±0.4° (p).

It is also favorable in accordance with the invention when the x-ray diffractogram additionally contains a reflection whose peak location is at the reflection angle (2Θ)=45.2±0.4° (q).

Frequently, the x-ray diffractogram of multimetal oxide active compositions to be used in accordance with the invention also contains the reflections 29.2±0.4° (m) and 35.4±0.4° (n) (peak locations).

If the intensity 100 is assigned to the reflection h, it is favorable in accordance with the invention when the reflections i, l, m, n, o, p, q in the same intensity scale have the following intensities:

i: from 5 to 95, frequently from 5 to 80, sometimes from 10 to 60;
l: from 1 to 30;
m: from 1 to 40;
n: from 1 to 40
o: from 1 to 30;
p: from 1 to 30 and
q: from 5 to 60.

When the x-ray diffractogram of the multimetal oxide active compositions to be used in accordance with the invention contains of [sic] the aforementioned additional reflections, the half-height width thereof is generally ≦1°.

The specific surface area of multimetal oxide active compositions to be used in accordance with the invention is in many cases from 1 to 40 m²/g, advantageously from 10, or 11, or 12 to 40 m²/g, and frequently from 15 or 20 to 40 or 30 m²/g (determined by the BET method, nitrogen).

Preference is given in accordance with the invention to using those multimetal oxide active compositions whose x-ray diffractogram has no reflection having the peak location 2Θ=50.0±0.3°.

All the data in this document relating to an x-ray diffractogram relates to an x-ray diffractogram obtained using Cu-Kα radiation as the x-ray radiation (Siemens Theta-Theta D-5000 diffractometer, tube voltage: 40 kV, tube current: 40 mA, aperture V20 (variable), collimator V20 (variable), secondary monochromator aperture (0.1 mm), detector aperture (0.6 mm), measuring interval (2Θ):0.02°, measuring time per step: 2.4 s, detector: scintillation counting tube; the definition of the intensity of a reflection in the x-ray diffractogram relates in this document to the definition laid down in DE-A 19835247, DE-A 10122027, and also in DE-A 10051419 and DE-A 10046672; the same applies to the definition of the half-height width).

It is particularly favorable in accordance with the invention to use catalytically active multimetal oxide active compositions to be used in accordance with the invention which satisfy the general stoichiometry I $$Mo_1V_aM^1{}_bM^2{}_cM^3{}_dO_n \qquad (1)$$

where
$M^1$=at least one of the elements from the group consisting of Te and Sb;
$M^2$=at least one of the elements from the group consisting of Nb, Ti, W, Ta and Ce;
$M^3$=at least one of the elements from the group consisting of Pb, Ni, Co, Bi, Pd, Fe, Mn, Ag, Pt, Cu, Au, Ga, Zn, Sn, In, Re, Ir, Sm, Sc, Y, Pr, Nd and Tb;
a=from 0.01 to 1,
b=from >0 to 1,
c=from >0 to 1,
d=from ≧0 to 0.5 (preferably from >0 to 0.5) and
n=a number which is determined by the valency and frequency of the elements in (I) other than oxygen.

The stoichiometric coefficient a of the multimetal oxide active compositions (I), irrespective of the preferred ranges for the other stoichiometric coefficients of the active multimetal oxide compositions (I), is preferably from 0.05 to 0.6, more preferably from 0.1 to 0.6 or 0.5.

Irrespective of the preferred ranges for the other stoichiometric coefficients of the multimetal oxide active compositions (I) to be used with preference in accordance with the invention, the stoichiometric coefficient b is preferably from 0.01 to 1, and more preferably from 0.01 or 0.05 or 0.1 to 0.5 or 0.4.

The stoichiometric coefficient c of the multimetal oxide active compositions (I) to be used advantageously in accordance with the invention, irrespective of the preferred ranges for the other stoichiometric coefficients of the multimetal oxide active compositions (I), is from 0.01 to 1 and more preferably from 0.01 or 0.1 to 0.5 or 0.4. A range for the stoichiometric coefficient c which is very particularly preferred in accordance with the invention and, irrespective of the preferred ranges for the other stoichiometric coefficients of the multimetal oxide active compositions (I) to be used in accordance with the invention, can be combined with all other preferred ranges in this document is the range from 0.05 to 0.2.

According to the invention, the stoichiometric coefficient d of the multimetal oxide active compositions (I) to be used in accordance with the invention, irrespective of the preferred ranges for the other stoichiometric coefficients of the multimetal oxide active compositions (I), is preferably from 0.00005 or 0.0005 to 0.5, more preferably from 0.001 to 0.5, frequently from 0.002 to 0.3 and often from 0.005 or 0.01 to 0.1.

It is particularly favorable when the stoichiometric coefficients a, b, c and d of multimetal oxide active compositions (I) to be used in accordance with the invention are simultaneously within the following pattern:
a=from 0.05 to 0.6;
b=from 0.01 to 1 (or from 0.01 to 0.5);
c=from 0.01 to 1 (or from 0.01 to 0.5); and
d=from 0.0005 to 0.5 (or from 0.001 to 0.3).

It is most favorable when the stoichiometric coefficients a, b, c and d of the multimetal oxide active compositions (I) to be used in accordance with the invention are simultaneously within the following pattern:
a=from 0.1 to 0.6;
b=from 0.1 to 0.5;
c=from 0.1 to 0.5; and d=from 0.001 to 0.5, or from 0.002 to 0.3, or from 0.005 to 0.1.

M1 is preferably Te.

All of the aforementioned is true in particular when at least 50 mol % of the total amount of $M^2$ is Nb and most preferably when at least 75 mol % of the total amount of $M^2$, or 100 mol % of its total amount, is Nb.

It is also true in particular, irrespective of the definition of $M^2$, when $M^3$ is at least one element from the group consisting of Pt, Fe, Re, Mn, Cu, Ni, Co, Bi, Pd, Ag, Au, Pb and Ga, or at least one element from the group consisting of Ni, Co, Pd, Pt, Fe and Bi.

All of the aforementioned is also true in particular when at least 50 mol % of the total amount of $M^2$, or at least 75 mol %, or 100 mol %, is Nb, and $M^3$ is at least one element from the group consisting of Pt, Fe, Re, Mn, Cu, Ni, Co, Bi, Pd, Ag, Au, Pb and Ga.

All of the aforementioned is also true in particular when at least 50 mol % of the total amount of $M^2$, or at least 75 mol %, or 100 mol %, is Nb, and $M^3$ is at least one element from the group consisting of Ni, Co, Pd, Pt, Fe and Bi.

Very particular preference is given to all statements relating to the stoichiometric coefficients being true when $M^1$=Te, $M^2$=Nb and $M^3$=at least one element from the group consisting of Ni, Co, Pt and Pd.

The principle of a selective process for preparing multimetal oxide active compositions to be used in accordance with the invention, in particular those of the general formula (I), is disclosed, for example, by WO 0206199 and the literature references cited in this document. According to this document, a multimetal oxide composition is initially obtained in a known manner and has the design stoichiometry, but is generally an intimately intertwined mixed crystal system composed of i phase and k phase. In this mixture, the fraction of i phase can then be increased or isolated by washing out the k phase with suitable liquids to the desired extent. Useful such liquids are, for example, organic acids and aqueous solutions of organic acids (e.g. oxalic acid, formic acid, acetic acid, citric acid and tartaric acid), inorganic acids (e.g. nitric acid), aqueous solutions of inorganic acids (e.g. aqueous telluric acid or aqueous nitric acid), alcohols and aqueous hydrogen peroxide solutions, Furthermore, JP-A 7-232071 also discloses a process for preparing i phase-rich multimetal oxide active compositions. Likewise suitable are the washing process of EP-A 1254707 and also of EP-A 1254706.

Mixed crystal systems composed of i and k phase are generally obtained by the preparative processes described in the prior art (cf., for example, DE-A 19835247, EP-A 529853, EP-A 603836, EP-A 608838, EP-A 895809, EP-A 962253, EP-A 1080784, EP-A 1090684, EP-A 1123738, EP-A 1192987, EP-A 1192986, EP-A 1192982, EP-A 1192983 and EP-A 1192988). In these processes, a very intimate, preferably finely divided dry mixture is obtained from suitable sources of the elemental constituents of the multimetal oxide composition and thermally treated at temperatures of from 350 to 700° C. or from 400 to 650° C. or 400 to 600° C. The thermal treatment may in principle be effected either under an oxidizing, a reducing or under an inert atmosphere. A useful oxidizing atmosphere is, for example, air, molecular oxygen-enriched air or oxygen-depleted air. However, preference is given to carrying out the thermal treatment under inert atmosphere, i.e., for example, under molecular nitrogen and/or noble gas. Typically, the thermal treatment is effected at atmospheric pressure (1 atm). It will be appreciated that the thermal treatment may also be effected under vacuum or under elevated pressure.

When the thermal treatment is effected under a gaseous atmosphere, it may either be stationary or flow. It preferably flows. Overall, the thermal treatment may take up to 24 h or more.

Preference is given to effecting the thermal treatment initially under an oxidizing (oxygen-containing) atmosphere (for example under air) at a temperature of from 150 to 400° C. or from 250 to 350° C. (=predecomposition step). Afterwards, the thermal treatment is appropriately continued under inert gas at temperatures of from 350 to 700° C. or from 400 to 650° C. or from 450 to 600° C. It will be appreciated that the thermal treatments may also be effected in such a way that the catalyst precursor composition., before its thermal treatment, may initially (optionally after pulverization) be tableted (optionally with the addition of from 0.5 to 2% by weight of finely divided graphite), then thermally treated and subsequently spalled again.

The intimate mixing of the starting compounds may be effected in dry or in wet form.

When it is effected in dry form, the starting compounds are appropriately used as finely divided powder and, after the mixing and optional compression, subjected to calcining (thermal treatment).

However, preference is given to effecting the intimate mixing in wet form. Typically, the starting compounds are mixed together in the form of an aqueous solution (optionally with the use of complexing agents; cf., for example, DE-A 10145958) and/or suspension. Subsequently, the aqueous composition is dried and, after the drying, calcined. The aqueous composition is appropriately an aqueous solution or an aqueous suspension. Preference is given to effecting the drying process immediately after the preparation of the aqueous mixture (especially in the case of an aqueous solution; cf., for example, JP-A 7-315842) and by spray drying (the exit temperatures are generally from 100 to 150° C.; the spray drying may be effected in cocurrent or in countercurrent), which requires a particularly intimate dry mixture, in particular when the aqueous composition to be spray-dried is an aqueous solution or suspension. However, it may also be dried by evaporation under reduced pressure, by freeze-drying or by conventional evaporation.

Useful sources for the elemental constituents when carrying out the above-described preparative method of i/k phase mixed crystal multimetal oxide compositions are all of those which are capable of forming oxides and/or hydroxides on heating (optionally under air). It will be appreciated that such starting compounds may partly or exclusively already be oxides and/or hydroxides of the elemental constituents. In other words, useful starting compounds are especially all of those mentioned in the documents EP-A 1254707, EP-A 1254709 and EP-A 1192987.

Suitable sources for the element Mo are, for example, molybdenum oxides such as molybdenumtrioxide, molybdates such as ammonium heptamolybdate tetrahydrate and molybdenum halides such as molybdenum chloride.

Suitable starting compounds for the element V are, for example, vanadium oxysulfate hydrate, vanadyl acetylacetonate, vanadates such as ammonium metavanadate, vanadium oxides such as vanadium pentoxide ($V_2O_5$), vanadium halides such as vanadium tetrachloride ($VCl_4$) and vanadium oxyhalides such as $VOCl_3$. The vanadium starting compounds used may also be those which contain the vanadium in the +4 oxidation state.

Suitable sources for the element tellurium are tellurium oxides such as tellurium dioxide, metallic tellurium, tellurium halides such as $TeCl_2$, but also telluric acids such as orthotelluric acid $H_6TeO_6$.

Advantageous antimony starting compounds are antimony halides such as $SbCl_3$, antimony oxides such as antimony trioxide ($Sb_2O_3$), antimony acids such as $HSb(OH)_6$, but also antimony oxide salts such as antimony oxide sulfate $(SbO)_2SO_4$ and also antimony acetate.

Suitable niobium sources are, for example, niobium oxides such as niobium pentoxide ($Nb_2O_5$), niobium oxide halides such as $NbOCl_3$, niobium halides such as $NbCl_5$, but also complexes of niobium and organic carboxylic acids and/or dicarboxylic acids, for example oxalates and alkoxides. It will be appreciated that the niobium source used may also be the Nb-containing solutions used in EP-A 895 809.

With regard to all other possible elements (in particular to Pb, Ni, Cu, Co, Bi and Pd), suitable starting compounds are in particular their halides, nitrates, formates, oxalates, acetates, carbonates and/or hydroxides. Suitable starting compounds are in many cases also their oxo compounds, for example tungstates or the acids derived therefrom. The starting compounds used are frequently also ammonium salts.

Also useful as starting compounds are polyanions of the Anderson type, as described, for example, in Polyhedron Vol. 6, No. 2, pp. 213-218, 1987. A further suitable literature source for polyanions of the Anderson type is Kinetics and Catalysis, Vol. 40, No. 3, 1999, pp 401 to 404.

Other polyanions suitable as starting compounds are, for example, those of the Dawson or Keggin type. Preference is given to using those starting compounds which are converted to their oxides at elevated temperatures either in the presence or with the exclusion of oxygen, optionally with the release of gaseous compounds.

The i/k phase mixed crystal multimetal oxide compositions (pure i phase multimetal oxides are obtained by chance, if at all, by the procedure described) obtainable as described may then be converted by suitable washing (in which the stoichiometry is generally changed only insignificantly) to active multimetal oxides to be used in accordance with the invention, in particular those of the stoichiometry (I). Preference is given to calcining again after the washing, as described in EP-A 1254709. The calcination conditions are generally the same as recommended for the preparation of the multimetal oxide composition to be washed.

An increased fraction of i phase (and in favorable cases substantially pure i phase) is attained in the preparation of precursor multimetal oxides (which can be converted by the washing described to multimetal oxides to be used in accordance with the invention, in particular those of the general formula (I)) when they are prepared by a hydrothermal route, as described, for example, by DE-A 10029338, DE-A 10254278 and JP-A 2000-143244. In this case too, recalcination can be effected according to EP-A 1254709.

However, active multimetal oxide compositions (I) to be used advantageously in accordance with the invention and having d>0 may also be prepared by initially obtaining a multimetal oxide composition I' which differs only from a multimetal oxide composition (I) in that d=0.

Such a preferably finely divided multimetal oxide composition I' may then be saturated with solutions (for example aqueous) of elements $M^3$ (for example by spraying), subsequently dried (preferably at temperatures $\leq 100°$ C.) and subsequently, as already described for the precursor multimetal oxides, calcined (preferably in an inert gas stream) (preference is given here to dispensing with predecomposition under air). The use of aqueous nitric acid and/or halide solutions of elements $M^3$ and/or the use of aqueous solutions in which the elements $M^3$ are present in complexed form with organic compounds (for example acetates or acetylacetonates), is particularly advantageous for this preparative variant.

The active multimetal oxides, in particular those of the formula (I), to be used in accordance with the invention and obtainable as described may be used as catalysts for the process according to the invention as such [for example as a powder or after tableting of the powder (frequently with the addition of from 0.5 to 2% by weight of finely divided graphite) and subsequent spalling to give spall] or else shaped to shaped bodies. The catalyst bed may be a fixed bed, a moving bed (a flowing bed) or a fluidized bed.

Shaping to shaped bodies may be effected, for example, by application to a support body, as described in DE-A 10118814 or PCT/EP/02/04073 or DE-A 10051419. Correspondingly, the procedure may also be that of DE-A 4442346.

The support bodies to be used for the active multimetal oxide compositions to be used in the process according to the invention, in particular those of the general formula (I), are preferably chemically inert. In other words, they substantially do not intervene in the course of the heterogeneously catalyzed gas phase partial oxidation according to the invention, which is catalyzed by the multimetal oxide compositions to be used in accordance with the invention, in particular those of the general formula (I).

According to the invention, useful material for the support bodies is in particular aluminum oxide, silicon dioxide, silicates such as clay, kaolin, steatite (preferably with a small water-soluble alkali metal content and preferably from Ceramtec in DE, for example steatite C220), pumice, aluminum silicate and magnesium silicate, silicon carbide, zirconium dioxide and thorium dioxide.

The surface of the support body may be either smooth or rough. Advantageously, the surface of the support body is rough, since an increased surface roughness generally causes increased adhesion of the active composition coating applied.

Frequently, the surface roughness $R_Z$ of the support body is generally from 5 to 200 μm, often in the range from 20 to 100 μm (determined to DIN 4768 sheet 1 with a "Hommel tester for DIN-ISO surface measurements" from Hommelwerke, Del.).

The support material may also be porous or nonporous. The support material is appropriately nonporous (total volume of the pores based on the volume of the support body $\leq 1\%$ by volume).

The thickness of the active oxide composition coating on the coated catalysts according to the invention is typically from 10 to 1000 μm. It may also be from 50 to 700 μm, from 100 to 600 μm or from 150 to 400 μm. Possible coating thicknesses are also from 10 to 500 μm, from 100 to 500 μm or from 150 to 300 μm.

In principle, the geometries of the support bodies for the process according to the invention may be as desired. Their longest dimension is generally from 1 to 10 mm. However, preference is given to employing spheres or cylinders, in particular hollow cylinders, as support bodies. Favorable diameters for support spheres are from 1.5 to 5 mm. When cylinders are used as support bodies, their length is preferably from 2 to 10 mm and their external diameter is preferably from 4 to 10 mm. In the case of rings, the wall thickness is additionally typically from 1 to 4 mm. Annular support bodies suitable in accordance with the invention may also have a length of from 3 to 6 mm, an external diameter of from 4 to 8 mm and a wall thickness of from 1 to 3 mm. However, a support ring geometry of 7 mm×3 mm×4 mm or of 5 mm×3 mm×2 mm (external diameter× length×internal diameter) is also possible.

Coated catalysts to be used in accordance with the invention may also be prepared in a simple manner for example, by preforming multimetal oxide active compositions to be used in accordance with the invention, in particular those of the general formula (I), converting them to finely divided form and finally applying them to the surface of the support body with the aid of a liquid binder. To this end, the surface of the support body is, in the simplest manner, moistened with the liquid binder and a layer of the active composition is attached to the moistened surface by contacting with finely divided active oxide composition, for example that of the general formula (I). Finally, the coated support body is dried. It will be appreciated that the procedure may be repeated periodically to achieve an increased layer thickness. In this case, the coated starting body becomes the new "support body", etc. On completion of coating, calcination may be repeated under the conditions already specified (preferably again under inert gas).

The fineness of the catalytically active multimetal oxide composition, for example that of the general formula (I), to be applied to the surface of the support body is of course adapted to the particular coating thickness. For the coating thickness range of from 100 to 500 μm, suitable active composition powders are, for example, those of which at least 50% of the total number of powder particles can pass through a sieve of mesh width from 1 to 20 μm and whose numerical fraction of particles having a longest dimension of above 50 mm is less than 10%. In general, the distribution of the longest dimensions of the powder particles, as a result of the production, corresponds to a Gaussian distribution. Frequently, the particle size distribution is as follows:

binder and serves to supply the finely divided oxidic active composition (for example via an agitated channel or a powder screw). The support spheres which have been moistened in a controlled manner take up the active composition powder supplied, which is compressed by the rolling movement to a continuous coating on the outer surface of the, for example cylindrical or spherical, support body.

If required, the support body basically coated in this way, in the course of the subsequent rotation, again passes through the spray nozzles, and is moistened in a controlled manner, in order, in the course of the further movement, to be able to take up a further layer of finely divided oxidic active composition, etc. (intermediate drying is generally not necessary). Finely divided oxidic active composition and liquid binder are generally supplied continuously and simultaneously.

The liquid binder may be removed on completion of coating, for example by the action of hot gases such as $N_2$ or air. Remarkably, the coating process described brings about fully satisfactory adhesion of the subsequent layers to each other and to the base layer on the surface of the support body.

It is essential for the above-described coating method that the moistening of the surface of the support body to be coated is carried out in a controlled manner. In short, this means that the support surface is appropriately moistened in such a way that, although it has adsorbed liquid binder, no liquid phase as such visibly appears on the support surface. When the support body surface is too moist, the finely divided catalytically active oxide composition agglomerates to separate agglomerates, instead of to the surface. Detailed information on this subject can be found in DE-A 2909671 and in DE-A 10051419.

The aforementioned final removal of the liquid binder used can be carried out in a controlled manner, for example by evaporation and/or sublimation. In the simplest case, this

| D (μm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| X | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

In the tables:
D = diameter of the particle,
X = the percentage of the particles whose diameter ≧ D; and
y = the percentage of the particles whose diameter < D.

For a performance of the coating process described on the industrial scale, it is recommended, for example, to employ the process principle disclosed in DE-A 2909671, and also that disclosed in DE-A 10051419. In other words, the support bodies to be coated are initially charged in a preferably tilted (the tilt angle is generally ≧0° and ≦90°, usually ≧30° and ≦90°; the tilt angle is the angle of the rotary vessel middle axis against the horizontal) rotating rotary vessel (for example rotary pan or coating drum). The rotating rotary vessel conducts the, for example spherical or cylindrical, support bodies under two metering devices arranged in succession at a certain separation. The first of the two metering devices is appropriately a nozzle (for example an atomizer nozzle operated with compressed air), through which the support bodies rolling in the rotating rotary vessel are sprayed with the liquid binder and moistened in a controlled manner. The second metering apparatus is disposed outside the atomization cone of the sprayed liquid may be effected by the action of hot gases at appropriate temperature (frequently from 50 to 300° C., frequently 150° C.). However, the action of hot gases may also be used only to bring about predrying. The final drying may then be effected, for example, in a drying oven of a known type (for example belt dryer) or in the reactor. The action temperature should not be above the calcination temperature employed to prepare the oxidic active composition. However, it will be appreciated that the drying may also be carried out exclusively in a drying oven.

The binder used for the coating process, irrespective of the type and the geometry of the support body, may be: water, monohydric alcohols such as ethanol, methanol, propanol and butanol, polyhydric alcohols such as ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, or else mono- or polyhydric organic amides such as formamide. Suitable binders are also solutions consisting of from 20 to 90% by weight of water and from 10 to 80% by weight of an organic compound dissolved in water whose boiling point or sublimation temperature at atmospheric pressure (1 atm) is >100° C., preferably >150° C. Advantageously, the organic compound is selected from the above listing of possible organic binders. The organic fraction of the aforementioned aqueous binder solutions is preferably from 10 to 50% by weight and more preferably from 20 to 30% by weight. Useful organic components are also monosaccharides and oligosaccharides such as glucose, fructose, sucrose or lactose, and also polyethylene oxides and polyacrylates.

It is significant that coated catalysts which are suitable in accordance with the invention can be prepared not only by applying the completed, finely ground active oxide compositions, for example of the general formula (I), to the moistened support body surface.

Rather, instead of the active oxide composition, a finely divided precursor composition thereof may also be applied to the moistened support surface (employing the same coating process and binder) and the calcination carried out after drying the coated support body (support bodies may also be impregnated with a precursor solution, consequently dried and subsequently calcined). Finally, the k phase different to the i phase may be washed out. Subsequently, calcination may be repeated in the manner described.

Such a finely divided precursor composition may be, for example, that composition which is obtainable by initially generating a very intimate, preferably finely divided dry mixture from the sources of the elemental constituents of the desired active oxide composition to be used in accordance with the invention, for example that of the general formula (I), (for example by spray drying an aqueous suspension or solution of the sources) and thermally treating thus finely divided dry mixture (optionally after tableting with the addition of 0.5 to 2% by weight of finely divided graphite) at a temperature of from 150 to 350° C., preferably from 250 to 350° C., under an oxidizing (oxygen-containing) atmosphere (for example under air) (a few hours) and finally, if required, subjecting it to grinding.

After the coating of the support bodies with the precursor composition, calcination is then effected, preferably under an inert gas atmosphere (all other atmospheres are also possible), at temperatures of from 360 to 700° C. or from 400 to 650° C. or from 400 to 600° C.

It will be appreciated that active multimetal oxide compositions which can be used in accordance with the invention, for example those of the general formula (I), may also be shaped by extrusion and/or tableting, either of finely divided multimetal oxide active composition or of finely divided precursor composition of a multimetal oxide active composition (if necessary, the phases other than the i phase may finally be washed out, optionally including a recalcination).

Suitable geometries are spheres, solid cylinders and hollow cylinders (rings). The longest dimension of the aforementioned geometries is generally from 1 to 10 mm. In the case of cylinders, their length is preferably from 2 to 10 mm and their external diameter is preferably from 4 to 10 mm. In the case of rings, the wall thickness is additionally typically from 1 to 4 mm. Annular unsupported catalysts suitable according to the invention may also have a length of from 3 to 6 mm, an external diameter of from 4 to 8 mm and a wall thickness of from 1 to 2 mm. However, an unsupported catalyst ring geometry of 7 mm×3 mm×4 mm or of 5 mm×3 mm×2 mm (external diameter×length×internal diameter) is also possible.

The geometries of the multimetal oxide active compositions to be used for the process according to the invention, in particular those of the general formula (I), may of course also be all of those of DE-A 10101695.

As already stated, it is essential to the invention that the multimetal oxide active compositions to be used in accordance with the invention, in particular those of the general formula I, have an x-ray diffractogram (in this document always based on Cu—Kα radiation) which has the reflections h, i and k whose peak locations are at the reflection angles (2Θ) 22.2+0.5° (h), 27.3+0.5° (i) and 28.2+0.5° (k), where the reflection h is the most intense within the x-ray diffractogram and has a half-height width of at most 0.5°, the intensity $P_i$ of the reflection i and the intensity $P_k$ of the reflection k satisfy the relationship 0.55≦R≦0.85 in which R is the intensity ratio defined by the formula $R=P_i/(P_i+P_k)$ and the half-height width of the reflection i and of the reflection k are each ≦1°.

At the same time, the x-ray diffractogram should more preferably have no reflection having the peak location 2Θ=50±0.3°.

In this document, the definition of the intensity of a reflection in the x-ray diffractogram relates, as already stated, to the definition laid down in DE-A 19835247, and also in DE-A 10051419 and DE-A 10046672.

In other words, if $A^1$ denotes the peak location of a reflection 1 and $B^1$, in the line of the x-ray diffractogram viewed along the intensity axis at right angles to the 2Θ axis, denotes the next pronounced minimum (minima showing reflection shoulders are not taken into account) to the left of the peak location $A^1$ and $B^2$ is correspondingly the next pronounced minimum to the right of the peak location $A^1$ and $C^1$ is the point at which a straight line drawn from the peak location $A^1$ at right angles to the 2Θ axis cuts a straight line joining the points $B^1$ and $B^2$, the intensity of the reflection 1 is the length of the straight line section $A^1C^1$ which then extends from the peak location $A^1$ to the point $C^1$. The expression minimum in this context means a point at which the slope of a tangent to the curve in a base region of the reflection 1 changes from a negative value to a positive value, or a point at which the slope tends to zero, using the coordinates of the 2Θ axis and of the intensity axis for the determination of the slope.

In this document, the half-height width is correspondingly the length of the straight line section between the two intersection points $H^1$ and $H^2$ when a line is drawn parallel to the 2Θ axis in the middle of the straight line section $A^1C^1$, $H^1$, $H^2$ meaning in each case the first point at which these parallel lines cut the line as defined above of the x-ray diffractogram to the left and right of $A^1$.

An exemplary execution of the determination of half-height width and intensity is also shown by FIG. 6 in DE-A 10046672.

It will be appreciated that the multimetal oxide active compositions to be used in accordance with the invention, in particular those of the general formula (I), may also be used as catalytic active compositions diluted with finely divided, for example colloidal, materials such as silicon dioxide, titanium dioxide, aluminum oxide, zirconium oxide, niobium oxide.

The dilution composition ratio may be up to 9 (diluent):1 (active composition). In other words, possible diluent composition ratios are, for example, 6 (diluent):1 (active composition) and 3 (diluent):1 (active composition). The diluent may be incorporated before and/or after the calcination, generally even before the drying. It is normally effected before the shaping.

When the incorporation is effected before the drying or before the calcination, the diluent has to be selected in such a way that it is substantially preserved in the fluid medium or in the calcination. This is the case, for example, for oxides calcined at appropriately high temperatures.

Otherwise, the process according to the invention, in particular in the case of a heterogeneously catalyzed gas phase partial oxidation of propane to acrylic acid, may be carried out as described in EP-A 608838, WO 0029106, JP-A 10-36311, DE-A 10316465 and EP-A 1192987.

The source used for the molecular oxygen required may be, for example, air, oxygen-enriched or oxygen-depleted air, or pure oxygen.

Otherwise, the starting reaction gas mixture, in addition to propane and molecular oxygen, and also steam, may comprise the inert diluent gases, for example, $N_2$, CO and $CO_2$.

In other words, the starting reaction gas mixture, with which the catalyst bed is to be charged at reaction temperatures of, for example, from 200 to 550° C. or from 230 to 480° C. or from 300 to 440° C., and pressures of from 1 to 10 bar, or from 2 to 5 bar (reduced pressure may in principle also be employed) may have, for example, the following contents:

from 1 to 15% by volume, preferably from 1 to 7% by volume, of propane,
from 5 to 25% by volume of steam and
from 10 to 80% by volume of air.

However, it may also have the following contents:
from 2 to 10% by volume of propane,
from 5 to 20% by volume of steam,
from 60 to 85% by volume of nitrogen, and
from 5 to 15% by volume of oxygen.

Multimetal oxide active compositions deactivated in the process according to the invention may be reactivated by passing over molecular oxygen- and/or steam-containing gases under the temperature and pressure conditions of the reaction causing the deactivation. Such a gas may be, for example, air, a mixture of air and steam, but also lean air (molecular oxygen-depleted air) or a mixture of steam and lean air. A mixture of nitrogen and steam may also be used. The oxygen content of the regeneration gas may therefore be from ≧0 to 20 mol %. It will frequently be from 2 to 10 mol %, sometimes from 2 to 15 mol %.

When the saturated hydrocarbon used in the process according to the invention is crude propane, it preferably has the composition as described in DE-A 10246119 or DE-A 10118814 or PCT/EP/02/04073.

A fresh catalyst charge may be brought on stream as described in DE-A 10122027.

When the process according to the invention is carried out over a fixed catalyst bed, it may be disposed, for example, in a tube bundle reactor whose catalyst tubes are flowed around by one or more independent heating media (for example salt baths) (in the latter case, this is referred to as a multizone reactor).

The temperature of the individual zones normally increases in the flow direction of the reaction gas mixture.

Suitable one-zone tube bundle reactors are described, for example, in EP-A 700714 and in EP-A 700893.

Multizone tube bundle reactors which are suitable in accordance with the invention are described, for example, in DE-A 19927624, DE-A 19948242, DE-A 19948241, DE-A 19910508 and in DE-A 19910506. An execution of the process according to the invention in a fluidized bed can be carried out, for example, as described in WO 02/0811421.

Based on the propane and/or isobutane present in the starting reaction gas mixture, the conversion of propane and/or isobutane in the process according to the invention, based on single pass of the reaction gas mixture through the catalyst bed, will generally be from 10 or 20 to 70 mol %, frequently from 30 to 60 mol % and in many cases from 40 to 60 mol % or from 45 to 55 mol %. The selectivity of target product formation will typically be from 40 to 98 or from 45 to 90 mol %, in many cases from 50 to 80 mol %, often from 60 to 80 mol %.

The target product removal and any cycle gas control may be effected as described in DE-A 10316465.

The hourly space velocity of propane and/or isobutane on the catalyst bed (not including inert beds) may be from 10 to 1000 l (STP)/l (catalyst bed)/h or from 20 to 800 l (STP)/l/h, or from 50 to 600 l (STP)/l/h, or from 100 to 500 l (STP)/l/h, or from 150 to 300 l (STP)/l/h.

The hourly space velocity of starting reaction gas mixture on the catalyst bed (not including inert beds) may be from 10 to 10 000 l (STP)/l/h, or from 300 to 6000 l (STP)/l/h, or from 300 to 2000 l (STP)/l/h. The average residence time in the catalyst charge may be from 0.01 s to 10 s, or from 0.1 to 10 s, or from 2 to 6 s.

EXAMPLES AND COMPARATIVE EXAMPLES

A) Preparation of a Multimetal Oxide Catalyst to Be Used in Accordance with the Invention.

1287.25 g of ammonium metavanadate (77.5% by weight of $V_2O_5$, from G.f.E., DE-Nuremberg) were dissolved at 80° C. in 44.6 l of water in a stainless steel vessel. A clear yellowish solution was formed. This solution was cooled to 60° C. and then, in succession in the sequence specified while maintaining the 60° C., first 1683.75 g of telluric acid (99% by weight of $H_6TeO_6$, from Fluka) and then 5868.0 g of ammonium heptamolybdate (81.5% by weight of $MoO_3$, from Starck) were stirred in. This resulted in a deep red solution A. In a second stainless steel vessel, 1599.0 g of ammonium niobium oxalate (21.1% by weight of Nb, Starck, DE-Goslar) were dissolved at 60° C. in 8.3 l of water to give a solution B. The two solutions, A and B, were cooled to 30° C. and combined at this temperature by stirring solution B into solution A. The stirring-in was effected continuously within a period of 10 minutes. This gave an orange-colored aqueous suspension.

This suspension was subsequently spray-dried ($T_{reservoir}$=30° C., $T^{in}$=240° C., $T^{out}$=110° C., drying time: 1.5 h, spray tower from Nipolosa). The resulting sprayed material was likewise orange-colored. 1% by weight of finely divided graphite (screen analysis: min. 50% by weight ≦24 μm, max. 10% by weight ≧24 μm and ≦48 μm, max. 5% by weight >48 μm, BET surface area: from 6 to 13 m²/g) was mixed into the sprayed material.

The resulting mixture was compacted (compressed) to hollow cylinders (rings) of geometry 16 mm×2.5 mm×8 mm (external diameter×height×internal diameter) in such a way that the resulting side crushing strength of the rings is approx. 10 N.

200 g of these rings were calcined in two portions each of 100 g in succession in a rotary kiln according to FIG. 1 of DE-A 10122027. To this end, the rotary kiln contents were heated from 25° C. to 275° C. under an airstream of 50 l (STP)/h with a linear heating ramp within 27.5 min, and kept at this temperature for 1 h while maintaining the airstream. Subsequently, heating was effected from 275° C. to 600° C. within 32.5 min with a linear heating ramp, the airstream having been replaced by a nitrogen stream of 50 l (STP)/h. The 600° C. and the nitrogen stream were maintained for 2 h and the entire kiln was subsequently left to cool to 25° C. while maintaining the nitrogen stream. This resulted in black tablets of the composition $Mo_{1.0}V_{0.33}Te_{0.15}Nb_{0.11}O_x$.

The tablets were then ground in the dry state in a Retsch mill to a particle size ≦100 μm. 150 g of the ground material were stirred in 1500 ml of a 10% by weight aqueous $HNO_3$ solution at 70° C. under reflux for 7 h, and the solids were filtered out of the resulting slurry and washed with water to free them of nitrate. The filtercake was dried at 110° C. in a muffle furnace under air overnight. The resulting active composition had the composition $Mo_{1.0}V_{0.27}Te_{0.12}Nb_{0.13}O_x$. Its x-ray diffractogram (cf. FIG. 1) revealed no pure i phase with R=0.74. It contained no reflection with the peak location 2Θ=50.0±0.3°.

75 g of the resulting active composition powder were applied to 300 g of spherical support bodies having a diameter of 2.2-3.2 mm (support material=steatite from Ceramtec, Del., total pore volume of the support ≦1% by volume based on the total support volume; $R_z$=45 μm). To this end, the support bodies were initially charged in a coating drum having a 2 l capacity (tilt angle of the drum center axis against the horizontal=30°). The drum was rotated at 25 revolutions per minute. An atomizer nozzle operated at 300 l (STP)/h of compressed air was used to spray about 30 ml of a mixture of glycerol and water (glycerol:water weight ratio=1:3) onto the support bodies over the course of 60 min. The nozzle was installed in such a way that the spray cone wetted the support bodies conveyed within the drum to the upper most point of the tilted drum by means of carrier plates, in the upper half of the roll-off section. The finely divided active composition powder was introduced into the drum via a powder screw, but the point of powder addition within the roll-off section was below the spray cone. The periodic repetition of wetting and powder replenishment resulted in the initially coated support body itself becoming the support body in the subsequent period.

On completion of coating, the coated support bodies were dried at 120° C. in a forced-air drying cabinet (Binder, DE, capacity 53 l) over 16 hours. Glycerol was removed by a subsequent two-hour heat treatment at 150° C. under air. A coated catalyst S20 to be used in accordance with the invention having a 20% by weight active composition fraction was obtained.

B) Experimental Procedure 35.0 g of the coated catalyst S20 were installed into a single-tube reactor (tube length: 140 cm, internal diameter: 8.5 mm, external diameter: 60 mm, V2A steel, catalyst bed length: 54.5 cm, additionally to heat the starting reaction gas mixture, a preliminary bed of length 30 cm of steatite spheres from Ceramtec (C220, diameter 2.2-3.2 mm); downstream of the catalyst zone, the reaction tube was finally filled with the same steatite spheres), which was heated by electrical heating mats. At a mat temperature of 350° C., the coated catalyst was installed into the tubular reactor under air.

Afterwards, the reaction tube was charged, while maintaining the mat temperature of 350° C., for 24 h with a starting reaction gas mixture (charging gas mixture) which had the following composition:

3.3% by volume of propane,
10% by volume of $O_2$,
40% by volume of $N_2$ and
46.7% by volume of $H_2O$.

The residence time (based on the catalyst bed volume) selected was 2.4 s, the reaction tube inlet pressure was 2 bar absolute and the GHSV was 1500 $h^{-1}$ (based on charging gas mixture).

Afterwards, in each case for 24 h, the composition of the charging gas mixture was changed and the mat temperature in each case adapted in such a way that the propane conversion, based on single reaction tube pass, was always approx. 40 mol %. The remaining boundary conditions were retained as described.

Between the individual charging gas mixture composition variants, the start-up composition was employed for in each case one hour, in order to ensure, as a reference point, that the catalyst bed had not been damaged. The mat temperature in this case was 390° C.

Depending on the charging gas mixture composition, the following results were obtained:

Comparative Example 1

Charging gas: 3.3% by vol. of propane; 10% by vol. of $O_2$; 40% by vol. of $N_2$; 46.7% by vol. of $H_2O$. At a mat temperature of 390° C., the propane conversion (based on single pass) was 40 mol %. The selectivity of acrylic acid formation was 71 mol %.

Comparative Example 2

Charging gas: 3.3% by vol. of propane; 10% by vol. of $O_2$; 86.7% by vol. of $N_2$; 0% by vol. of $H_2O$. At a mat temperature of 410° C., a propane conversion of 41 mol % and a selectivity of acrylic acid formation of 45 mol % were achieved.

Comparative Example 3

Charging gas: 3.3% by vol. of propane; 10% by vol. of $O_2$; 70% by vol. of $N_2$; 16.7% by vol. of $H_2O$. At a mat temperature of 390° C. a propane conversion of 40 mol % and a selectivity of acrylic acid formation of 70 mol % were achieved.

Comparative Example 4

Charging gas: 3.3% by vol. of propane; 3.3% by vol. of $O_2$; 76.7% by vol. of $N_2$; 16.7% by vol. of $H_2O$. At a mat temperature of 415° C. a propane conversion of 41 mol % and a selectivity of acrylic acid formation of 68 mol % were achieved.

Example 1

Charging gas: 3.3% by vol. of propane; 8.0% by vol. of $O_2$; 72.0% by vol. of $N_2$; 16.7% by vol. of $H_2O$. At a mat temperature of 390° C. a propane conversion of 40 mol % and a selectivity of acrylic acid formation of 70 mol % were achieved.

Example 2

Charging gas: 3.3% by vol. of propane; 6.0% by vol. of $O_2$; 74% by vol. of $N_2$; 16.7% by vol. of $H_2O$. At a mat temperature of 395° C. a propane conversion of 40 mol % and a selectivity of acrylic acid formation of 72 mol % were achieved.

Example 3

Charging gas: 3.3% by vol. of propane; 8.0% by vol. of $O_2$; 82.7% by vol. of $N_2$; 6.0% by vol. of $H_2O$. At a mat temperature of 400° C. a propane conversion of 39 mol % and a selectivity of acrylic acid formation of 70 mol % were achieved.

Example 4

Charging gas: 5.0% by vol. of propane; 10.0% by vol. of $O_2$; 68.3% by vol. of $N_2$; 16.7% by vol. of $H_2O$. At a mat temperature of 395° C. a propane conversion of 40 mol % and a selectivity of acrylic acid formation of 71 mol % were achieved.

U.S. Provisional Patent Application No. 60/496,015, filed on Aug. 19, 2003, is incorporated into the present application by way of reference. With reference to the abovementioned teachings, numerous alterations and deviations from the present invention are possible. It may therefore be assumed that the invention, within the scope of the appended claims, may be performed differently from the way specifically described herein.

We claim:

1. A process for preparing (meth)acrylic acid by heterogeneously catalyzed gas phase partial oxidation of at least one saturated hydrocarbon precursor compound, by charging a catalyst bed which is disposed in a reactor and whose catalytically active composition is a multimetal oxide which contains the elements Mo and V, one or both of the elements Te and Sb, and one or more elements selected from the group consisting of Nb, Ta, W, Ce and Ti, and whose x-ray diffractogram has reflections h, i and k whose peak locations are at the reflection angles (2Θ) 22.2±0.5° (h), 27.3±0.50° (i) and 28.2±0.5° (k), where the reflection h is the most intense within the x-ray diffractogram and has a half-height width of at most 0.50°, the intensity $P_i$ of the reflection i and the intensity $P_k$ of the reflection k satisfy the relationship 0.55≦R≦0.85 in which R is the intensity ratio defined by the formula $$R=P_i/(P_i+P_k)$$

and the half-height width of the reflection i and of the reflection k are each ≦1°, at elevated temperature with a charging gas mixture which, in addition to the at least one saturated hydrocarbon precursor compound, molecular oxygen as an oxidant and steam as a promoter, also comprises at least one diluent gas which is substantially inert under the conditions of the heterogeneously catalyzed gas phase partial oxidation, wherein the steam content of the charging gas mixture is from 5 to 25% by volume and the molar ratio V of molecular oxygen present in the charging gas mixture to the at least one saturated hydrocarbon precursor compound present in the charging gas mixture is from 1.5:1 to 2.5:1.

2. A process as claimed in claim 1, wherein the steam content of the charging gas mixture is from 10 to 20% by volume.

3. A process as claimed in claim 1, wherein V is from 1.75:1 to 2.25:1.

4. A process as claimed in claim 1, wherein the oxygen source used is air.

5. A process as claimed in claim 1, wherein 0.65≦R≦0.85 is satisfied.

6. A process as claimed in claim 1, wherein 0.69≦R≦0.74 is satisfied.

7. A process as claimed in claim 1, wherein 0.71≦R≦0.73 is satisfied.

8. A process as claimed in claim 1, wherein R=0.72.

9. A process as claimed in claim 1, wherein the x-ray diffractogram also contains further reflections whose peak locations are at the following reflection angles:

9.0±0.4° (l),
6.7±0.4° (o) and
7.9±0.4° (p).

10. A process as claimed in claim 1, wherein the x-ray diffractogram also contains a reflection angle q whose peak location is at the reflection angle 45.2±0.4°.

11. A process as claimed in claim 1, wherein the x-ray diffractogram also contains further reflections whose peak locations are at the following reflection angles:

29.2±0.40° (m),
35.4±0.40° (n).

12. A process as claimed in claim 1, wherein the x-ray diffractogram contains reflections h, i, k, l, m, n, o, p and q which have the following relative intensities in the same intensity scale:

h: 100,
i: from 5 to 95,
l: from 1 to 30,
m: from 1 to 40,
n: from 1 to 40,
o: from 1 to 30,
p: from 1 to 30 and
q: from 5 to 60.

13. A process as claimed in claim 1, wherein the specific surface area of the active multimetal oxide composition is from 10 to 40 $m^2/g$.

14. A process as claimed in claim 1, wherein the x-ray diffractogram has no reflection having the peak location 2Θ=50.0±0.3°.

15. A process as claimed in claim 1, wherein the active multimetal oxide composition is one of the stoichiometry

$$Mo_1V_aM^1_bM^2_cM^3_dO_n \qquad (I)$$

where $M^1$=at least one of the elements from the group consisting of Te and Sb;

$M^2$=at least one of the elements from the group consisting of Nb, Ti, W, Ta and Ce;

at least one of the elements from the group consisting of Pb, Ni, Co, Bi, Fe, Mn, Pd, Ag, Pt, Cu, Au, Ga, Zn, Sn, In, Re, Ir, Sm, Sc, Y, Pr, Nd and Tb;

a=from 0.1 to 1,
b=from >0 to 1,
c=from >0 to 1,
d=from ≧0 to 0.5 and
n=a number which is determined by the valency and frequency of the elements in (I) other than oxygen.

16. A process as claimed in claim 15, wherein d>0.

17. A process as claimed in claim 15, wherein d is from 0.00005 to 0.5.

18. A process as claimed in claim 1, wherein the catalyst bed comprises coated catalysts.

19. A process as claimed in claim 1, which is carried out at reaction temperatures of from 200 to 550° C.

20. A process as claimed in claim 1, which is carried out at a reaction pressure of from 1 to 10 bar.

21. A process as claimed in claim 1, wherein the conversion of the hydrocarbon precursor compound on single pass through the catalyst bed is from 30 to 60 mol %.

22. A process as claimed in claim 1, wherein the hourly space velocity of propane on the catalyst bed is from 10 to 1000 l (STP)/l/h.

\* \* \* \* \*